United States Patent
Nagl et al.

[11] Patent Number: 5,932,727
[45] Date of Patent: Aug. 3, 1999

[54] PROCESS FOR THE PREPARATION OF DIOXAZINE COMPOUNDS

[75] Inventors: Gert Nagl, Niederdorfelden; Wolfgang Bauer, Maintal; Manfred Urban, Wiesbaden; Dieter Schnaitmann, Eppstein, all of Germany

[73] Assignee: Clariant GmbH, Frankfurt, Germany

[21] Appl. No.: 08/951,689

[22] Filed: Oct. 16, 1997

[30] Foreign Application Priority Data

Oct. 21, 1996 [DE] Germany ............... 196 43 344

[51] Int. Cl.⁶ .................................................. C09B 19/02
[52] U.S. Cl. .................................................. 544/99
[58] Field of Search ................................. 544/99

[56] References Cited

U.S. PATENT DOCUMENTS

| | | | |
|---|---|---|---|
| 3,826,746 | 7/1974 | Schick | 252/51.5 |
| 4,345,074 | 8/1982 | Hufnagel et al. | 544/99 |
| 4,504,666 | 3/1985 | Earl et al. | 546/345 |
| 4,997,937 | 3/1991 | Tzikas | 544/99 |
| 5,149,807 | 9/1992 | Hammond | 544/99 |

FOREIGN PATENT DOCUMENTS

| | | |
|---|---|---|
| 0 036 966 | 10/1981 | European Pat. Off. . |
| 0234870 | 9/1987 | European Pat. Off. ............ 544/99 |
| 2 587 705 | 3/1987 | France . |
| 56-141355 | 11/1981 | Japan . |
| 62-192385 | 8/1987 | Japan . |
| H5-43808 | 2/1993 | Japan . |
| H6-179682 | 6/1994 | Japan . |
| H7-145327 | 6/1995 | Japan . |

OTHER PUBLICATIONS

Derwent abstract: XP-002053097 (1988).
Derwent abstract: XP-002053098 (1987).
Derwent abstract: XP-002053099 (1981).
Derwent abstract: XP-002053100 (1993).
Maki et al Tetrahedron vol. 44 pp. 1187–1194 (1988.

*Primary Examiner*—Donald G. Daus
*Attorney, Agent, or Firm*—Susan S. Jackson

[57] ABSTRACT

The present invention relates to a process for the preparation of dioxazine derivatives of the formula I

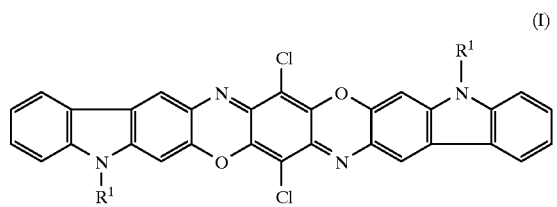

(I)

in which $R^1$ is hydrogen or $(C_1-C_8)$-alkyl, by ring closure of a compound of the formula II

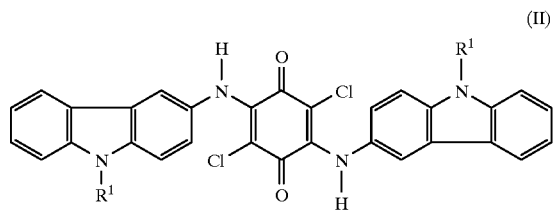

(II)

in the presence of a ring-closure agent, wherein the ring-closure agent used is an N-hetarene N-oxide. The compounds of the formula I are used for producing valuable dyes and pigments.

11 Claims, No Drawings

PROCESS FOR THE PREPARATION OF DIOXAZINE COMPOUNDS

The present invention relates to an improved process for the preparation of dioxazine compounds of the formula I

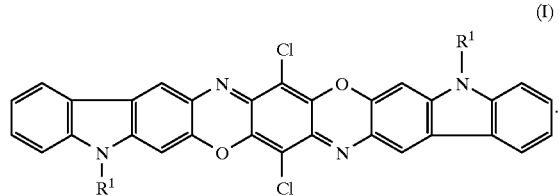

These dioxazine compounds are used for preparing valuable dyes and pigments (see Ullmann's Encyclopedia of Industrial Chemistry, Vol. A 3, p. 233) and can be prepared industrially for example by ring closure of compounds of the formula II

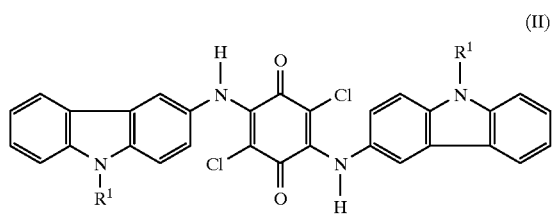

using benzenesulfonyl chloride or 4-toluenesulfonyl chloride as ring-closure agent (see U.S. Pat. No. 4,345,074).

Other ring-closure agents that have been proposed are benzenesulfonyl chlorides which have electrophilic substituents on the benzene ring (see JP Hei 7-145327). It is also already known that the yield can be improved by carrying out the ring closure in the presence of a phase transfer catalyst (see JP Sho 56-141355) or an organic base (see JP Hei 6-179682). Ring closure under reduced pressure has also already been described (see JP Hei 5-43808). In the cited documents, the yields obtained are at best 87% of theory (see Examples 1 and 3 of JP Hei 543808).

A disadvantage in all methods in which the ring-closure agent used is benzenesulfonyl chloride or its derivatives is the fact that a large quantity of non-utilizable waste is produced from the ring-closure agent. The quantity of waste is increased all the more by the fact that the achievable yield still falls a long way short of theory. The resulting need for improvement as regards conserving resources and relieving the impact on the environment has already been recognized. For example, JP Sho 62-192385 proposes heterocyclic amines, which can be recovered, as ring-closure agents for this purpose. Some of the waste is avoided as a result, but the products prepared in this way contained substantially less chlorine than calculated from the formula (I). In addition, it was not possible to increase the yield to the required values.

It is thus the object to provide a ring closure process for the preparation of the dioxazine compounds of the formula (I) which satisfies the following criteria: ring closure should be effected using a ring-closure agent which does not produce any waste, and the product should be produced in a form which can be filtered very easily, and, in the finish, gives a pigment with high tinctorial strength, a pure reddish hue and very good fastness properties.

Surprisingly, it has been found that the dioxazine compounds of the formula (I) can be prepared whilst satisfying the said criteria if the ring-closure agent used is an N-hetarene N-oxide instead of benzenesulfonyl chloride or toluenesulfonyl chloride.

The present invention thus relates to a process for the preparation of dioxazine derivatives of the formula I

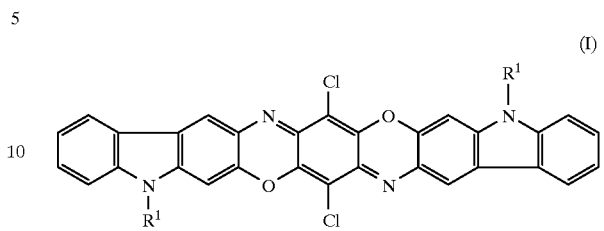

in which $R^1$ is hydrogen or $(C_1-C_8)$-alkyl, by ring closure of a compound of the formula II

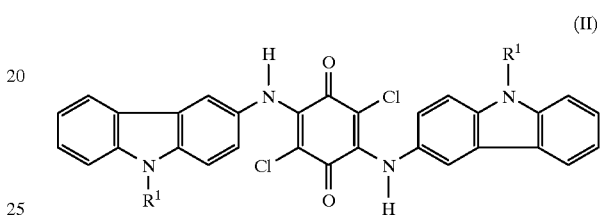

in the presence of a ring-closure agent, wherein the ring-closure agent used is an N-hetarene N-oxide.

$(C_1-C_8)$-alkyl $R^1$ can be straight-chain or branched and may, for example, be methyl, ethyl, n-propyl, isopropyl, n-butyl, sec-butyl, isobutyl, tert-butyl, pentyl, hexyl, heptyl or octyl. Ethyl is preferred.

Examples of suitable hetarene N-oxides are compounds of the formula III

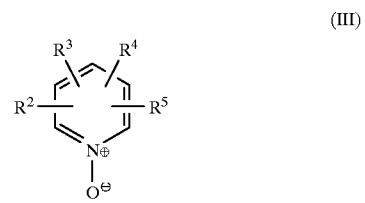

in which $R^2$, $R^3$, $R^4$ and $R^5$, independently of one another, are hydrogen, $(C_1-C_4)$-alkyl, chlorine or cyano, compounds of the formula IV or IVa

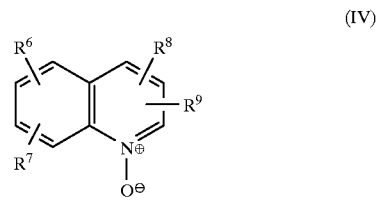

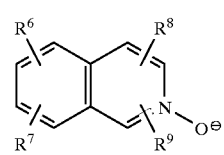

in which $R^6$, $R^7$, $R^8$ and $R^9$, independently of one another, are hydrogen or $(C_1-C_4)$-alkyl, and compounds of the formula V

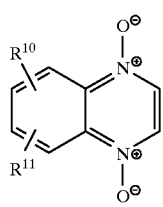

in which $R^{10}$ and $R^{11}$, independently of one another, are hydrogen or $(C_1-C_4)$-alkyl.

$(C_1-C_4)$-alkyl radicals $R^2$ to $R^{11}$ can be straight-chain or branched and may, for example, be methyl, ethyl, n-propyl, isopropyl, n-butyl, sec-butyl, isobutyl or tert-butyl.

Particularly preferred hetarene N-oxides are those which are cheap and can readily be prepared on an industrial scale. Examples are pyridine N-oxide and the N-oxides of the various picolines. Pyridine N-oxide is particularly preferred. The N-hetarene N-oxides are reduced in the ring closure reaction to give N-hetarene and water. If the N-hetarene formed boils below the reaction temperature, it can be distilled off from the reaction mixture during the reaction and then reoxidized by known methods to give the N-hetarene N-oxide, for example as in U.S. Pat. Nos. 3,826,746, 4,504,666 and EP-A 224662.

The N-hetarene N-oxides can be used in pure form or as a mixture or as solutions in inert organic solvents or in water. The quantity of N-hetarene N-oxide added can be varied within wide limits. Preferably, the N-hetarene N-oxide is added in a quantity of from 1 to 3 mol, based on 1 mol of the compound of the formula II. Quantities of from 1.2 to 2.5 mol, based on 1 mol of the compound of the formula II, are particularly preferred.

We have found that the yield of the compound of the formula I can be increased almost to theory if the process according to the invention is carried out in the presence of a quinone. In a preferred embodiment of the process according to the invention, the ring closure reaction is therefore carried out in the presence of a quinone compound. The quinone compound used can be any quinone which is described in the literature as a dehydrogenating agent. Quinones which are cheap and which can readily be prepared on an industrial scale are preferred. p-Benzoquinone is particularly preferred and chloranil is very particularly preferred. The quantity of quinone added can be varied within wide limits. Although larger quantities are not detrimental to the reaction, relatively little is added in order to keep the amount of waste very low. The quinone is preferably used in a quantity of from 5 to 50 mol percent, based on the compound of the formula II. A quinone quantity of from 10 to 40 mol percent is particularly preferred.

The ring closure reaction according to the invention is preferably carried out at temperatures between 150° C. and 200° C. Suitable reaction media are inert organic solvents with correspondingly high boiling points. Examples of suitable solvents are alkylbenzenes, dialkylbenzenes, alkylnaphthalenes, alkanes, alkenes, o-dichlorobenzene, m-dichlorobenzene and p-dichlorobenzene. The preferred reaction medium is o-dichlorobenzene. The reaction can also be carried out under reduced pressure. The rate of reaction is comparable with conventional ring closure using benzenesulfonyl chlorides. For example, in boiling o-dichlorobenzene, ring closure is practically complete after, at most, three hours.

At the end of the reaction time, the reaction mixture is usually filtered while still hot and the paste obtained is washed with hot solvent and dried. In order to remove any water-soluble byproducts which may have been produced in small quantities, the product is usually extracted with water.

The compounds of the formula II can for example be prepared in a manner known per se by condensation of 3-amino-N-alkyl-carbazoles of the formula VI

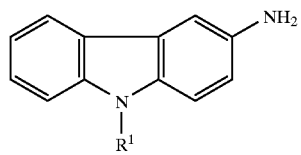

in which $R^1$ is as defined above, with chloranil in an inert organic solvent. Examples of inert organic solvents that can be used are alkylbenzenes, dialkylbenzenes, alkylnaphthalenes, alkanes and alkenes (see for example JP Hei-7-331097 and JP Hei-7-331098).

The compound of the formula II obtained by this process can, in the form of the suspension obtained, be subjected directly, i.e. without isolation, to the ring closure reaction according to the invention. If the condensation reaction is carried out with an excess of chloranil, it is not necessary to add further quinone to the ring closure reaction.

The present invention also relates to a process for the preparation of dioxazine derivatives of the formula I

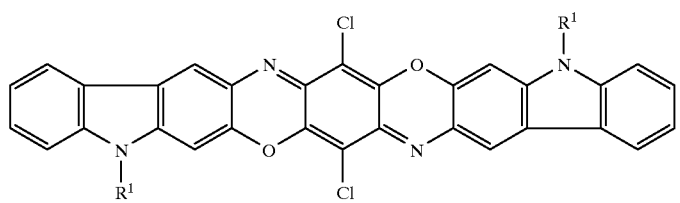

in which $R^1$ is hydrogen or $(C_1-C_8)$-alkyl, by condensation of a 3-amino-N-alkylcarbazole of the formula VI

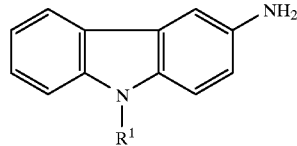

in which $R^1$ is as defined above, with chloranil in an inert organic solvent to give a condensation product of the formula II

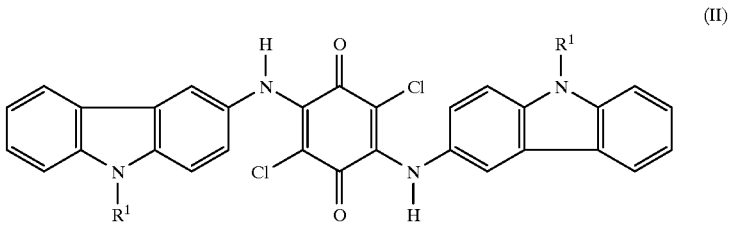

(II)

and subsequent ring closure to give the compound of the formula I in the presence of a ring-closure agent, wherein the ring-closure agent used is an N-hetarene N-oxide.

Examples of inert organic solvents which may be used are alkylbenzenes, dialkylbenzenes, alkylnaphthalenes, alkanes and alkenes. o-Dichlorobenzene is preferred.

Chloranil is preferably used in quantities of from 0.50 to 0.75 mol, particularly preferably 0.55 to 0.65 mol, per mole of the compound of the formula VI.

The following examples serve to explain the process according to the invention in more detail.

EXAMPLE 1

41.6 g of 2,5-dichloro-3,6-bis(9-ethyl-3-carbazolylamino)-1,4-benzoquinone are slurried in 390 g of o-dichlorobenzene in a 500 ml four-neck flask with precision glass paddle stirrer, dropping funnel, thermometer, distillation bridge and oil bath. The mixture is heated to the boiling point. A solution of 15 g of pyridine N-oxide in 15 g of o-dichlorobenzene is then added dropwise over the course of half an hour with stirring and distillation. The mixture is then stirred for a further three hours with further distillation. A total of approximately 100 ml distill off. The reaction mixture is filtered while still hot. The paste is washed with 500 g of hot o-dichlorobenzene and dried at 100° C. in vacuo. The dried material is stirred in 500 g of water at approximately 60° C., filtered and washed with water. Drying gives 33.6 g of the dioxazine compound of the formula I in which $R^1$ is an ethyl group (81.3% of theory). The identity of this compound was confirmed by IR absorption spectra, X-ray diffraction, testing as pigment and elemental analysis.

EXAMPLE 2

41.6 g of 2,5-dichloro-3,6-bis(9-ethyl-3-carbazolylamino)-1,4-benzoquinone are slurried in 390 g of o-dichlorobenzene in a 500 ml four-neck flask with precision glass paddle stirrer, dropping funnel, thermometer, distillation bridge and oil bath. 5.7 g of chloranil are added and the mixture is heated to boiling point. A solution of 12.0 g of pyridine N-oxide in 12 g of o-dichlorobenzene is added dropwise over the course of 15 minutes with stirring and distillation. The mixture is then further stirred for three hours with further distillation. A total of approximately 100 ml distill off. The reaction mixture is filtered while still hot. The paste is washed with 500 g of hot o-dichlorobenzene and dried at 100° C. in vacuo. The dried material is stirred in 500 g of water at approximately 60° C., filtered and washed with water. Drying gives 40.7 g of the dioxazine compound of the formula I in which $R^1$ is an ethyl group (98.5% of theory). The identity of this compound was confirmed by IR absorption spectra, X-ray diffraction, testing as pigment and elemental analysis.

EXAMPLES 3–7

Example 2 was repeated but using other N-hetarene N-oxides or other quinone compounds instead of pyridine N-oxide and/or instead of chloranil. The yield of the dioxazine compound of the formula I in which $R^1$ is an ethyl group is shown in Table 1:

TABLE 1

| Example | N-Hetarene N-oxide (quantity) | Quinone (quantity) | Yield in g | Yield (% in theory) |
|---|---|---|---|---|
| 3 | Pyridine N-oxide (14 g) | p-Benzoquinone (2 g) | 35.0 | 84.7 |
| 4 | Pyridine N-oxide (14 g) | 2,3-Dichloro-1,4-naphthoquinone (4 g) | 34.5 | 83.5 |
| 5 | 2-Picoline-N-oxide (14 g) | Chloranil (5.5 g) | 39.4 | 95.3 |
| 6 | 4-Picoline-N-oxide (15 g) | Chloranil (4 g) | 37.7 | 91.2 |
| 7 | 4-Picoline-N-oxide (15 g) | p-Benzoquinone (2 g) | 39.1 | 94.6 |

Comparative Example 1 (conventional process):

41.6 g of 2,5-dichloro-3,6-bis(9-ethyl-3-carbazolylamino)-1,4-benzoquinone are slurried in 390 g of o-dichlorobenzene in a 500 ml four-neck flask with precision glass paddle stirrer, thermometer, distillation bridge and oil bath. 17 g of benzenesulfonyl chloride are added and the mixture is heated to the boiling point. The mixture is then stirred for three hours with distillation. A total of approximately 100 ml distill off. The reaction mixture is filtered while still hot. The paste is washed with 500 g of hot o-dichlorobenzene and dried at 100° C. in vacuo. The dried material is stirred in 500 g of water at approximately 60° C., filtered and washed with water. Drying gives 34.7 g of the dioxazine compound of the formula I in which $R^1$ is an ethyl group (84.0% of theory).

EXAMPLE 8

840 g of a 7.5% technical-grade solution of 3-amino-9-ethylcarbazole in o-dichlorobenzene are placed in a 1000 ml four-neck flask with precision glass paddle stirrer, dropping funnel, thermometer, distillation apparatus and oil bath. 39 g of chloranil and 16 g of soda are added and then the mixture is stirred at 30–65° C. until no more 3-amino-9-ethylcarbazole can be detected by TLC. The water of reaction is distilled off by heating to 160° C. and the mixture is heated further at the boiling point. A solution of 32 g of pyridine N-oxide in 32 g of o-dichlorobenzene is then added dropwise over the course of half an hour with stirring and distillation. The mixture is then further stirred for three hours with further distillation. A total of approximately 250 ml distill off. The reaction mixture is filtered while still hot. The paste is washed with 1000 g of o-dichlorobenzene and dried at 100° C. in vacuo. The dried material is stirred in 1000 g of water at approximately 60° C., filtered and washed with water. Drying gives 73.3 g of the dioxazine compound of the formula I in which $R^1$ is an ethyl group (82.9% of theory). The identity of this compound was confirmed using IR absorption spectra, X-ray diffraction, testing as pigment and elemental analysis.

EXAMPLE 9

840 g of a 7.5% technical-grade solution of 3-amino-9-ethylcarbazole in o-dichlorobenzene are placed in a 1000 ml four-neck flask with precision glass paddle stirrer, dropping funnel, thermometer, distillation apparatus and oil bath. 39 g of chloranil and 16 g of soda are added and then the mixture is stirred at 30–65° C. until no more 3-amino-9-ethylcarbazole can be detected by TLC. The water of reaction is distilled off by heating to 160° C., 4.5 g of chloranil are then added and the mixture is heated to the boiling point. A solution of 25 g of pyridine N-oxide in 25 g of o-dichlorobenzene is then added dropwise over the course of half an hour with stirring and distillation. The mixture is then further stirred for three hours with further distillation. A total of approximately 250 ml distill off. The reaction mixture is filtered while still hot. The paste is washed with 1000 g of hot o-dichlorobenzene and dried at 100° C. in vacuo. The dried material is stirred in 1000 g of water at approximately 60° C., filtered and washed with water. Drying gives 79.1 g of the dioxazine compound of the formula I in which $R^1$ is an ethyl group (89.4% of theory). The identity of this compound is confirmed by IR absorption spectra, X-ray diffraction, testing as pigment and elemental analysis.

EXAMPLE 10

Example 9 is repeated, the only difference being that 9 g of chloranil are added to the mixture. 86.1 g of the dioxazine compound of the formula I in which $R^1$ is an ethyl group is obtained (97.4% of theory). The identity of this compound was confirmed by IR absorption spectra, X-ray diffraction, testing as pigment and elemental analysis.

EXAMPLE 11

840 g of a 7.5% technical-grade solution of 3-amino-9-ethylcarbazole in o-dichlorobenzene are placed in a 1000 ml four-neck flask With precision glass paddle stirrer, dropping funnel, thermometer, distillation apparatus and oil bath. 39 g of chloranil and 16 g of soda are added and then the mixture is stirred at 30–65° C. until no more 3-amino-9-ethylcarbazole can be detected by TLC. The water of reaction is distilled off by heating to 160° C., and then 9 g of chloranil and 25 g of pyridine N-oxide are added. The mixture is further heated to the boiling point. 210 ml distill off in one hour. 210 ml of o-dichlorobenzene are then added dropwise over the course of 2 hours, and 210 ml distill off at the same time. The mixture is then filtered while still hot. The paste is washed with 1000 g of hot o-dichlorobenzene and dried at 100° C. in vacuo. The dried material is stirred in 1000 g of water at approximately 60° C., filtered and washed with water. Drying gives 84.5 g of the dioxazine compound of the formula I in which $R^1$ is an ethyl group (95.5% of theory). The identity of this compound was confirmed by IR absorption spectra, X-ray diffraction, testing as pigment and elemental analysis.

EXAMPLE 12

840 g of a 7.5% technical-grade solution of 3-amino-9-ethylcarbazole in o-dichlorobenzene are placed in a 1000 ml four-neck flask with precision glass paddle stirrer, dropping funnel, thermometer, distillation apparatus and oil bath. 39 g of chloranil and 16 g of soda are added and then the mixture is stirred at 30–65° C. until no more 3-amino-9-ethylcarbazole can be detected by TLC. The water of reaction is distilled off by heating to 160° C.; 4.5 g of p-benzoquinone are then added and the mixture is heated to the boiling point. A solution of 35 g of 4-picoline N-oxide in 35 g of o-dichlorobenzene is then added dropwise over the course of half an hour with stirring and distillation. The mixture is then further stirred for three hours with further distillation. A total of approximately 250 ml distill off. The reaction mixture is filtered while still hot. The paste is washed with 1000 g of hot o-dichlorobenzene and dried at 100° C. in vacuo. The dried material is stirred into 1000 g of water at approximately 60° C., filtered and washed with water. Drying gives 84.7 g of the dioxazine compound of the formula I in which $R^1$ is an ethyl group (95.8% of theory). The identity of this compound was confirmed by IR absorption spectra, X-ray diffraction, testing as pigment and elemental analysis.

Comparative Example 2 (conventional process):

840 g of a 7.5% technical-grade solution of 3-amino-9-ethylcarbazole in o-dichlorobenzene are placed in a 1000 ml four-neck flask with precision glass paddle stirrer, thermometer, distillation apparatus and oil bath. 39 g of chloranil and 16 g of soda are added and then the mixture is stirred at 30–65° C. until no more 3-amino-9-ethylcarbazole can be detected by TLC. The water of reaction is distilled off by heating to 160° C. and 35 g of benzenesulfonyl chloride are then added. The mixture is further heated to the boiling point and then stirred for 3 hours with distillation. The mixture is then filtered while still hot. The paste is washed with 1000 g of hot o-dichlorobenzene and dried at 100° C. in vacuo. The dried material is stirred into 1000 g of water at approximately 60° C., filtered and washed with water. Drying gives 76.3 g of the dioxazine compound of the formula I in which $R^1$ is an ethyl group (86.3% of theory).

Use Example 1

22.5 parts of the dioxazine compound of the formula I in which $R^1$ is an ethyl group, prepared according to one of the above examples, and 7.5 parts of anhydrous sodium sulfate are introduced into a plastic container which is filled to 90% by volume with 1400 parts of cylindrical grinding media (Cylpebs®, diameter 12 mm, manufacturer: Groh GmbH, Hof). The mixture is finely ground for 4 hours with shaking on a vibratory mill (model Vibratom; manufacturer: Siebtechnik Mühlheim). The ground product is then sieved off from the grinding media. 25.9 parts of ground product are obtained.

37.5 parts of isobutanol (85%) are placed in a stirred vessel, and 2.5 parts of 98% formic acid and then 0.38 parts of the sodium salt of an alkylphenol polyglycol ether sulfate are added. 25 parts of the above ground product are then introduced and the mixture is stirred at 20 to 25° C. for 20 hours. During this time, another 50 parts of 85% isobutanol are added. 150 parts of water are then added; the mixture is heated at the boiling point for 5 hours and the isobutanol is distilled off azeotropically at the transition by heating to 100° C. After the mixture has cooled to 60° C., the pigment is filtered off with suction, washed with water until neutral and salt-free and dried at 80° C. 18.6 parts of a pigment are obtained which, in the alkyd-melamine resin coating, give transparent and intense violet finishes with a red tinge. The overcoating fastness is satisfactory. In nitrocellulose intaglio printing, transparent and intensely colored prints with high gloss are obtained.

Use Example 2

30 parts of the dioxazine compound of the formula I in which $R^1$ is an ethyl group, prepared according to one of the above examples, are introduced into a plastic container which is filled to 90% by volume with 1400 parts of cylindrical grinding media (Cylpebs®, diameter 12 mm, manufacturer: Groh GmbH, Hof). The crude pigment is finely ground for 4 hours with shaking on a vibratory mill (model: Vibratom; manufacturer: Siebtechnik Mühlheim). The ground product is then sieved off from the grinding media. 25.9 parts of ground product are obtained. 37.5 parts of isobutanol (85%) are placed in a stirred vessel, and 1.25 parts of 98% formic acid are added. 25 parts of the above ground product are then introduced and the mixture is stirred at 20 to 25° C. for 20 hours. During this time, another 50 parts of 85% isobutanol are added. 150 parts of water are then added, and the isobutanol is distilled off azeotropically at the transition by heating to 100° C. After the mixture has cooled to 60° C., the pigment is filtered off with suction, washed with water until neutral and dried at 80° C.

24.2 parts of a pigment are obtained which, in PVC, gives transparent and intense violet colorations. The bleeding fastness is very good.

We claim:

1. A process for the preparation of a dioxazine compound of the formula I

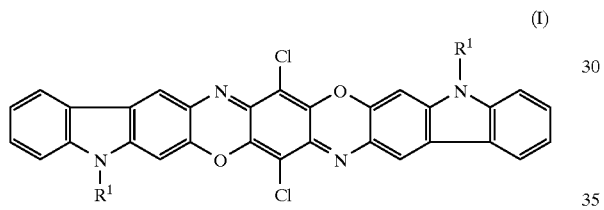

in which $R^1$ is hydrogen or $(C_1-C_8)$-alkyl, by ring closure of a compound of the formula II

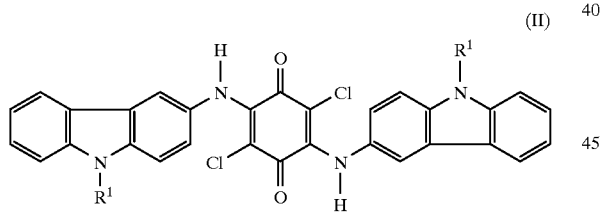

in the presence of a ring-closure agent, wherein the ring-closure agent used is an N-hetarene N-oxide compound selected from the group consisting of a compound of the formula III

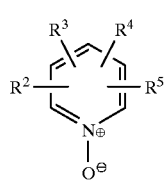

in which $R^2$, $R^3$, $R^4$ and $R^5$, independently of one another, are hydrogen, methyl, ethyl, n-propyl, isopropyl, n-butyl, sec-butyl, isobutyl, chlorine or cyano, a compound of the formula IV or IVa

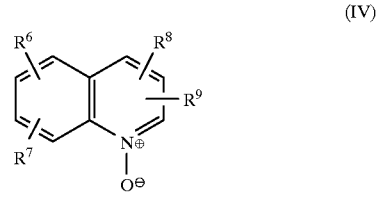

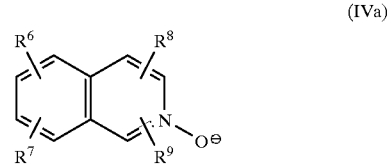

in which $R^6$, $R^7$, $R^8$ and $R^9$, independently of one another, are hydrogen, methyl, ethyl, n-propyl, isopropyl, n-butyl, sec-butyl, isobutyl, and a compound of the formula V

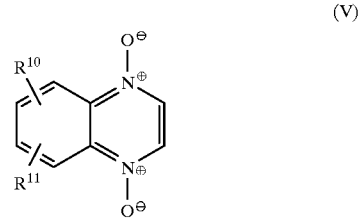

in which $R^{10}$ and $R^{11}$, independently of one another, are hydrogen, methyl, ethyl, n-propyl, isopropyl, n-butyl, sec-butyl, isobutyl.

2. The process as claimed in claim 1, wherein $R^1$ is ethyl.

3. The process as claimed in claim 1, wherein the N-hetarene N-oxide used is pyridine N-oxide or a picoline N-oxide.

4. The process as claimed in claim 1, wherein the N-hetarene N-oxide is used in quantities of from 1 to 3 mol, per mole of the compound of the formula II.

5. The process as claimed in claim 1, wherein the N-hetarene N-oxide is used in quantities of from 1.2 to 2.5 mol, per mole of the compound of the formula II.

6. The process as claimed in claim 1, which is carried out in the presence of a quinone compound.

7. The process as claimed in claim 6, wherein the quinone compound use is p-benzoquinone or chloranil.

8. The process as claimed in claim 6, wherein the quinone compound is used in quantities of from 5 to 50 mol percent based on the compound of the formula II.

9. The process as claimed in claim 6, wherein the quinone compound is used in quantities of from 10 to 40 mol percent based on the compound of the formula II.

10. The process for the preparation of a dioxazine compound of the formula I

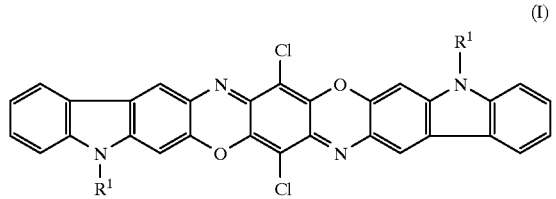

(I)

in which R¹ is hydrogen or (C₁–C₈)-alkyl, by condensation of a 3-amino-N-alkylcarbazole of the formula VI

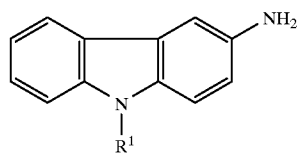

(VI)

in which R¹ is as defined above, with chloranil in an inert organic solvent to give a condensation product of the formula II

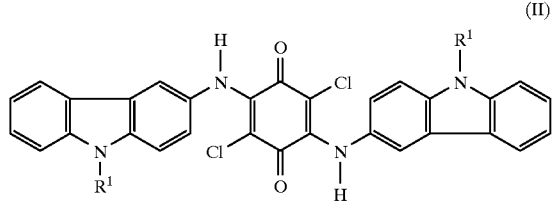

(II)

and subsequent ring-closure to give a compound of the formula I, in the presence of a ring-closure agent, wherein the ring-closure agent used is an N-hetarene N-oxide compound selected from the group consisting of a compound of the formula III

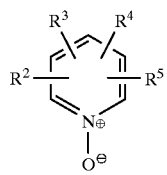

(III)

in which $R^2$, $R^3$, $R^4$ and $R^5$, independently of one another, are hydrogen, methyl, ethyl, n-propyl, isopropyl, n-butyl, sec-butyl, isobutyl, chlorine or cyano, a compound of the formula IV or IVa

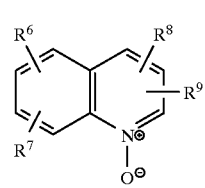

(IV)

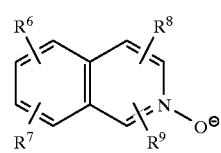

(IVa)

in which $R^6$, $R^7$, $R^8$ and $R^9$, independently of one another, are hydrogen, methyl, ethyl, n-propyl, isopropyl, n-butyl, sec-butyl, isobutyl, and a compound of the formula V

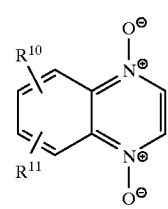

(V)

in which $R^{10}$ and $R^{11}$, independently of one another, are hydrogen, methyl, ethyl, n-propyl, isopropyl, n-butyl, sec-butyl, isobutyl.

11. The process as claimed in claim 10, wherein the compound of the formula II is not isolated.

* * * * *